(12) United States Patent
Bansal et al.

(10) Patent No.: US 11,918,762 B2
(45) Date of Patent: Mar. 5, 2024

(54) REDUCED ACTUATION FORCE ELECTROPHYSIOLOGY CATHETER HANDLE

(71) Applicant: St. Jude Medical, Cardiology Division, Inc., St. Paul, MN (US)

(72) Inventors: Varun D. Bansal, Plymouth, MN (US); Michael S. Bowers, Edina, MN (US); Alexandre Ioan Romoscanu, Geneva (CH)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1067 days.

(21) Appl. No.: 16/591,304

(22) Filed: Oct. 2, 2019

(65) Prior Publication Data
US 2020/0108228 A1    Apr. 9, 2020

Related U.S. Application Data

(60) Provisional application No. 62/740,828, filed on Oct. 3, 2018.

(51) Int. Cl.
*A61M 25/01*         (2006.01)
*A61B 17/00*         (2006.01)
(Continued)

(52) U.S. Cl.
CPC ..... *A61M 25/0136* (2013.01); *A61B 18/1492* (2013.01); *A61M 25/0147* (2013.01);
(Continued)

(58) Field of Classification Search
CPC ............ A61M 25/0147; A61M 25/008; A61M 25/0136; A61M 25/0133; A61M 25/015; A61M 25/0105; A61B 18/1492; A61B 2017/003; A61B 2017/00867; A61B 2017/00318; A61B 2018/0091;
(Continued)

(56) References Cited

U.S. PATENT DOCUMENTS

| 4,998,916 A | 3/1991 | Hammerslag et al. |
| 5,037,391 A | 8/1991 | Hammerslag et al. |

(Continued)

FOREIGN PATENT DOCUMENTS

| CN | 101927053 B | 1/2015 |
| CN | 103157168 B | 4/2015 |

(Continued)

*Primary Examiner* — Khadijeh A Vahdat
*Assistant Examiner* — Marina Delaney Templeton
(74) *Attorney, Agent, or Firm* — Kilpatrick Townsend & Stockton LLP (57) ABSTRACT

A uni-directional, plunger-type electrophysiology catheter handle is designed to reduce the input force a user must apply to deflect the distal end of the catheter. A force amplifier is operatively coupled to a deflection actuator of the handle. The force amplifier can be a pulley or a system of gears. The force amplifier can increase the output force of deflection actuator by the same factor as that by which the user input force is reduced. A variable-friction autolocking system can also be used to reduce the input force a user must apply during initial deflection as compared to later deflection of the catheter.

18 Claims, 11 Drawing Sheets

(51) Int. Cl.
*A61B 18/00* (2006.01)
*A61B 18/14* (2006.01)

(52) U.S. Cl.
CPC .............. *A61B 2017/003* (2013.01); *A61B 2018/00351* (2013.01); *A61B 2018/00952* (2013.01)

(58) Field of Classification Search
CPC ........... A61B 2018/00946; A61B 2018/00952; A61B 2018/0231; A61B 2017/00327; A61B 2018/00351
See application file for complete search history.

(56) References Cited

U.S. PATENT DOCUMENTS

| | | |
|---|---|---|
| 5,108,368 A | 4/1992 | Hammerslag et al. |
| 5,224,939 A | 7/1993 | Holman et al. |
| 5,290,229 A | 3/1994 | Paskar |
| 5,308,324 A | 5/1994 | Hammerslag et al. |
| 5,329,923 A | 7/1994 | Lundquist |
| 5,364,352 A | 11/1994 | Cimino et al. |
| 5,380,301 A | 1/1995 | Prichard et al. |
| 5,383,923 A | 1/1995 | Webster, Jr. |
| 5,389,073 A | 2/1995 | Imran |
| 5,391,147 A | 2/1995 | Imran et al. |
| 5,400,783 A | 3/1995 | Pomeranz et al. |
| 5,423,771 A | 6/1995 | Imran |
| 5,456,254 A | 10/1995 | Pietroski et al. |
| 5,626,136 A | 5/1997 | Webster, Jr. |
| 5,656,029 A | 8/1997 | Imran et al. |
| 5,715,817 A | 2/1998 | Stevens-Wright et al. |
| 5,827,278 A | 10/1998 | Webster, Jr. |
| 5,857,997 A | 1/1999 | Cimino et al. |
| 5,861,024 A | 1/1999 | Rashidi |
| 5,876,373 A | 3/1999 | Giba et al. |
| 5,987,344 A | 11/1999 | West |
| 6,013,052 A | 1/2000 | Durman et al. |
| 6,074,379 A | 6/2000 | Prichard |
| 6,198,974 B1 | 3/2001 | Webster, Jr. |
| 6,254,568 B1 | 7/2001 | Ponzi |
| 6,273,404 B1 | 8/2001 | Holman et al. |
| 6,491,681 B1 | 12/2002 | Kunis et al. |
| 6,530,913 B1 | 3/2003 | Giba et al. |
| 6,554,794 B1 | 4/2003 | Mueller et al. |
| 6,652,506 B2 | 11/2003 | Bowe et al. |
| 7,004,937 B2 | 2/2006 | Lentz et al. |
| 7,214,220 B2 | 5/2007 | McGlinch et al. |
| 7,217,256 B2 | 5/2007 | Di Palma |
| 7,374,553 B2 | 5/2008 | Koerner et al. |
| 7,608,063 B2 | 10/2009 | Le et al. |
| 7,625,365 B2 | 12/2009 | McGlinch et al. |
| 7,666,204 B2 | 2/2010 | Thornton et al. |
| 7,959,601 B2 | 6/2011 | McDaniel et al. |
| 7,985,215 B2 | 7/2011 | Guo et al. |
| 8,103,327 B2 | 1/2012 | Harlev et al. |
| 8,137,321 B2 | 3/2012 | Argentine |
| 8,162,934 B2 | 4/2012 | Potter |
| 8,177,741 B2 | 5/2012 | Hammack et al. |
| 8,221,390 B2 | 7/2012 | Pal et al. |
| 8,273,016 B2 | 9/2012 | O'Sullivan |
| 8,376,990 B2 | 2/2013 | Ponzi et al. |
| 8,447,377 B2 | 5/2013 | Harlev et al. |
| 8,465,442 B2 | 6/2013 | Freed |
| 8,608,703 B2 | 12/2013 | Riles et al. |
| 8,649,880 B1 | 2/2014 | Parker, Jr. |
| 8,700,120 B2 | 4/2014 | Koblish |
| 8,706,193 B2 | 4/2014 | Govari et al. |
| 8,755,861 B2 | 6/2014 | Harlev et al. |
| 8,777,929 B2 | 7/2014 | Schneider et al. |
| 8,792,962 B2 | 7/2014 | Esguerra et al. |
| 8,814,824 B2 | 8/2014 | Kauphusman et al. |
| 8,814,825 B2 | 8/2014 | Tegg et al. |
| 8,882,705 B2 | 11/2014 | McDaniel et al. |
| 8,894,610 B2 | 11/2014 | Macnamara et al. |
| 8,996,091 B2 | 3/2015 | de la Rama et al. |
| 9,017,308 B2 | 4/2015 | Klisch et al. |
| 9,033,917 B2 | 5/2015 | Magana et al. |
| 9,050,010 B2 | 6/2015 | Bui et al. |
| 9,101,733 B2 | 8/2015 | McDaniel |
| 9,204,929 B2 | 12/2015 | Solis |
| 9,216,056 B2 | 12/2015 | Datta et al. |
| 9,247,990 B2 | 2/2016 | Kauphusman et al. |
| 9,326,815 B2 | 5/2016 | Watson |
| 9,339,631 B2 | 5/2016 | Graham et al. |
| 9,433,751 B2 | 9/2016 | Ponzi et al. |
| 9,433,752 B2 | 9/2016 | Jimenez et al. |
| 9,468,495 B2 | 10/2016 | Kunis et al. |
| 9,486,280 B2 | 11/2016 | Koblish et al. |
| 9,486,282 B2 | 11/2016 | Solis |
| 9,539,413 B2 | 1/2017 | Ogle |
| 9,649,158 B2 | 5/2017 | Datta et al. |
| 9,687,166 B2 | 6/2017 | Subramaniam et al. |
| 9,693,733 B2 | 7/2017 | Altmann et al. |
| 9,694,159 B2 | 7/2017 | Schneider et al. |
| 9,694,161 B2 | 7/2017 | Selkee |
| 9,788,895 B2 | 10/2017 | Solis |
| 9,820,664 B2 | 11/2017 | Hoitink et al. |
| 9,844,645 B2 | 12/2017 | Pai et al. |
| 9,848,795 B2 | 12/2017 | Marecki et al. |
| 9,919,132 B2 | 3/2018 | Tegg et al. |
| 9,949,656 B2 | 4/2018 | Wu et al. |
| 9,986,949 B2 | 6/2018 | Govari et al. |
| 10,004,877 B2 | 6/2018 | Tegg |
| 10,034,637 B2 | 7/2018 | Harlev et al. |
| 10,052,457 B2 | 8/2018 | Nguyen et al. |
| 10,065,019 B2 | 9/2018 | Hamuro et al. |
| 10,099,036 B2 | 10/2018 | Heideman et al. |
| 10,118,021 B2 | 11/2018 | Bansal et al. |
| 10,118,022 B2 | 11/2018 | Helgeson et al. |
| 10,143,394 B2 | 12/2018 | Solis |
| 10,322,261 B2 | 6/2019 | Pai et al. |
| 10,362,952 B2 | 7/2019 | Basu et al. |
| 10,362,954 B2 | 7/2019 | de la Rama et al. |
| 10,376,170 B2 | 8/2019 | Quinn et al. |
| 10,384,036 B2 | 8/2019 | Romoscanu |
| 10,398,500 B2 | 9/2019 | Huszar et al. |
| 10,478,325 B2 | 11/2019 | Syed |
| 10,506,938 B2 | 12/2019 | Wu et al. |
| 10,537,259 B2 | 1/2020 | Wu et al. |
| 10,542,899 B2 | 1/2020 | Wu et al. |
| 10,556,091 B2 | 2/2020 | Truhler et al. |
| 10,575,742 B2 | 3/2020 | Wu et al. |
| 10,575,745 B2 | 3/2020 | Solis |
| 10,595,738 B2 | 3/2020 | Sterrett et al. |
| 10,595,740 B2 | 3/2020 | Hoitink et al. |
| 10,602,948 B2 | 3/2020 | Wu et al. |
| 10,646,692 B2 | 5/2020 | Tegg et al. |
| 10,653,423 B2 | 5/2020 | Starnes |
| 10,702,677 B2 | 7/2020 | Okamura et al. |
| 10,737,060 B2 | 8/2020 | Gupta et al. |
| 10,835,712 B2 | 11/2020 | Wada |
| 10,842,990 B2 | 11/2020 | de la Rama et al. |
| 10,857,349 B2 | 12/2020 | de la Rama et al. |
| 10,869,992 B2 | 12/2020 | Pai et al. |
| 10,898,685 B2 | 1/2021 | Tegg |
| 10,912,925 B2 | 2/2021 | Houck |
| 10,945,626 B2 | 3/2021 | Fuentes-ortega et al. |
| 10,946,167 B2 | 3/2021 | Mintz et al. |
| 10,953,196 B2 | 3/2021 | Raab et al. |
| 10,959,636 B2 | 3/2021 | Dahlen et al. |
| 10,966,623 B2 | 4/2021 | Wu et al. |
| 10,966,753 B2 | 4/2021 | Coyle et al. |
| 10,967,150 B2 | 4/2021 | Helgeson et al. |
| 10,987,045 B2 | 4/2021 | Basu et al. |
| 11,033,715 B2 | 6/2021 | Beeckler et al. |
| 11,039,772 B2 | 6/2021 | Wu et al. |
| 11,039,773 B2 | 6/2021 | Sterrett et al. |
| 11,083,400 B2 | 8/2021 | Hoitink et al. |
| 11,116,436 B2 | 9/2021 | Wu et al. |
| 11,116,476 B2 | 9/2021 | Buesseler et al. |
| 11,123,051 B2 | 9/2021 | Van Der Linde et al. |
| 11,141,568 B2 | 10/2021 | Hsueh et al. |
| 11,160,482 B2 | 11/2021 | Solis |

(56) References Cited

U.S. PATENT DOCUMENTS

| | | |
|---|---|---|
| 11,172,858 B2 | 11/2021 | Olson et al. |
| 11,272,886 B2 | 3/2022 | Harlev et al. |
| 2001/0041891 A1 | 11/2001 | Thompson et al. |
| 2002/0165484 A1 | 11/2002 | Bowe et al. |
| 2005/0187455 A1 | 8/2005 | Rashidi |
| 2006/0074383 A1 | 4/2006 | Boulais |
| 2006/0100640 A1 | 5/2006 | Bolduc |
| 2007/0016164 A1 | 1/2007 | Dudney et al. |
| 2007/0156116 A1 | 7/2007 | Gonzalez |
| 2011/0257499 A1 | 10/2011 | de la Rama et al. |
| 2012/0089125 A1 | 4/2012 | Scheibe et al. |
| 2012/0197236 A1 | 8/2012 | Randolph |
| 2012/0203170 A1 | 8/2012 | Potter |
| 2012/0209143 A1 | 8/2012 | Schultz |
| 2013/0018307 A1 | 1/2013 | Lee et al. |
| 2013/0096553 A1 | 4/2013 | Hill et al. |
| 2013/0144209 A1 | 6/2013 | Ryan |
| 2013/0172813 A1 | 7/2013 | Caples et al. |
| 2014/0100639 A1 | 4/2014 | Lee et al. |
| 2014/0276222 A1 | 9/2014 | Tegg |
| 2014/0276645 A1 | 9/2014 | Lam |
| 2015/0119911 A1 | 4/2015 | Mckenzie |
| 2016/0213423 A1 | 7/2016 | Kauphusman et al. |
| 2016/0278851 A1 | 9/2016 | Mannion et al. |
| 2016/0325076 A1* | 11/2016 | Terwey .............. A61M 25/0136 |
| 2016/0331933 A1 | 11/2016 | Knutsen |
| 2017/0065415 A1* | 3/2017 | Rupp .................... A61F 2/2433 |
| 2017/0319269 A1 | 11/2017 | Oliverius et al. |
| 2017/0367756 A1 | 12/2017 | Sliwa et al. |
| 2018/0042667 A1 | 2/2018 | Pappone et al. |
| 2018/0085064 A1 | 3/2018 | Auerbach et al. |
| 2018/0161093 A1 | 6/2018 | Basu et al. |
| 2018/0200416 A1* | 7/2018 | Oza ...................... A61B 1/2733 |
| 2018/0229030 A1 | 8/2018 | Dubuclet et al. |
| 2018/0369574 A1 | 12/2018 | Dubuclet et al. |
| 2019/0009052 A1 | 1/2019 | Oliverius et al. |
| 2019/0125378 A1 | 5/2019 | Shelton, IV et al. |
| 2019/0192826 A1 | 6/2019 | Wada |
| 2020/0077908 A1 | 3/2020 | Hagfors et al. |
| 2020/0121894 A1 | 4/2020 | Prabhu et al. |
| 2020/0138378 A1 | 5/2020 | de La Rama et al. |
| 2020/0214635 A1 | 7/2020 | Dahlen et al. |
| 2020/0253496 A1 | 8/2020 | Deno et al. |
| 2020/0405166 A1 | 12/2020 | Wu et al. |
| 2021/0016062 A1* | 1/2021 | Sarabia ............. A61M 25/0662 |
| 2021/0038860 A1 | 2/2021 | Mintz et al. |
| 2021/0145342 A1 | 5/2021 | Wang |
| 2021/0153932 A1 | 5/2021 | Voth et al. |
| 2021/0187246 A1 | 6/2021 | Houck |
| 2021/0204871 A1 | 7/2021 | Goedeke et al. |
| 2021/0268234 A1 | 9/2021 | Helgeson et al. |
| 2021/0298656 A1 | 9/2021 | Wu et al. |
| 2021/0361216 A1 | 11/2021 | Hoitink et al. |
| 2021/0401345 A1 | 12/2021 | Wu et al. |
| 2022/0023594 A1 | 1/2022 | Pai |
| 2022/0054066 A1 | 2/2022 | Solis |
| 2022/0061727 A1 | 3/2022 | Olson et al. |

FOREIGN PATENT DOCUMENTS

| | | |
|---|---|---|
| CN | 106859765 A | 6/2017 |
| CN | 206880930 U | 1/2018 |
| CN | 104958824 B | 12/2018 |
| CN | 104434083 B | 4/2019 |
| CN | 104968261 B | 5/2019 |
| CN | 105592778 B | 7/2019 |
| CN | 110536646 A | 12/2019 |
| CN | 110604860 A | 12/2019 |
| CN | 111225627 A | 6/2020 |
| CN | 111432739 A | 7/2020 |
| CN | 111657866 A | 9/2020 |
| CN | 106264715 B | 11/2020 |
| CN | 106264716 B | 11/2020 |
| CN | 112040861 A | 12/2020 |
| CN | 106308790 B | 6/2021 |
| CN | 107529958 B | 7/2021 |
| CN | 109310469 B | 7/2021 |
| CN | 109641121 B | 9/2021 |
| CN | 109952123 B | 9/2021 |
| CN | 110545874 B | 9/2021 |
| CN | 110559544 B | 9/2021 |
| CN | 113425304 A | 9/2021 |
| CN | 105615994 B | 10/2021 |
| CN | 109963610 B | 11/2021 |
| CN | 108289709 B | 3/2022 |
| EP | 0600676 A2 | 6/1994 |
| EP | 0616794 A1 | 9/1994 |
| EP | 0452402 B1 | 6/1995 |
| EP | 0790066 A2 | 8/1997 |
| EP | 0868923 A3 | 5/1999 |
| EP | 0889744 B1 | 1/2004 |
| EP | 0980693 B1 | 1/2005 |
| EP | 1254641 B1 | 11/2008 |
| EP | 2002859 A2 | 12/2008 |
| EP | 1690564 B1 | 4/2009 |
| EP | 1832307 B1 | 4/2010 |
| EP | 1723981 B1 | 8/2010 |
| EP | 1803481 B1 | 9/2010 |
| EP | 2135634 B1 | 10/2011 |
| EP | 2438954 A1 | 4/2012 |
| EP | 2018203 B1 | 6/2012 |
| EP | 1814450 B1 | 1/2013 |
| EP | 2269532 B1 | 3/2013 |
| EP | 2583616 A1 | 4/2013 |
| EP | 2609886 A2 | 7/2013 |
| EP | 2604306 B1 | 1/2014 |
| EP | 2915555 A1 | 9/2015 |
| EP | 1968679 B1 | 9/2016 |
| EP | 2241279 B1 | 9/2016 |
| EP | 3115076 A4 | 10/2017 |
| EP | 3117863 A4 | 10/2017 |
| EP | 3111871 B1 | 3/2018 |
| EP | 3111872 B1 | 4/2018 |
| EP | 3057488 B1 | 5/2018 |
| EP | 2848226 B1 | 7/2018 |
| EP | 3363397 A1 | 8/2018 |
| EP | 3391928 A1 | 10/2018 |
| EP | 3122276 B1 | 11/2018 |
| EP | 3398549 A1 | 11/2018 |
| EP | 1759668 B1 | 12/2018 |
| EP | 3037122 B1 | 12/2018 |
| EP | 2234537 B1 | 1/2019 |
| EP | 2569040 B1 | 2/2019 |
| EP | 3023052 B1 | 3/2019 |
| EP | 3466363 A1 | 4/2019 |
| EP | 2550989 B1 | 6/2019 |
| EP | 3512589 A1 | 7/2019 |
| EP | 3512590 A1 | 7/2019 |
| EP | 3527125 A1 | 8/2019 |
| EP | 3531903 A1 | 9/2019 |
| EP | 3581229 A1 | 12/2019 |
| EP | 3434218 B1 | 2/2020 |
| EP | 2908723 B1 | 3/2020 |
| EP | 3114987 B1 | 8/2020 |
| EP | 3178516 B1 | 9/2020 |
| EP | 3738508 A1 | 11/2020 |
| EP | 3738509 A1 | 11/2020 |
| EP | 3340916 B1 | 12/2020 |
| EP | 3579908 B1 | 12/2020 |
| EP | 3749195 A1 | 12/2020 |
| EP | 3750475 A1 | 12/2020 |
| EP | 3768185 A1 | 1/2021 |
| EP | 2155301 B1 | 4/2021 |
| EP | 3432820 B1 | 4/2021 |
| EP | 3476331 B1 | 5/2021 |
| EP | 3579758 B1 | 5/2021 |
| EP | 2809254 B1 | 6/2021 |
| EP | 3508245 B1 | 7/2021 |
| EP | 3858277 A1 | 8/2021 |
| EP | 3892221 A1 | 10/2021 |
| EP | 3932343 A4 | 1/2022 |
| EP | 3791820 B9 | 4/2022 |
| JP | 07255855 A | 10/1995 |
| JP | 4545384 B2 | 7/2010 |

(56) References Cited

FOREIGN PATENT DOCUMENTS

| | | |
|---|---|---|
| JP | 4887810 B2 | 2/2012 |
| JP | 4940332 B2 | 3/2012 |
| JP | 2012055602 A | 3/2012 |
| JP | 2012200509 A | 10/2012 |
| JP | 5154031 B2 | 2/2013 |
| JP | 5193190 B2 | 5/2013 |
| JP | 5372314 B2 | 12/2013 |
| JP | 2014014713 A | 1/2014 |
| JP | 5550150 B2 | 5/2014 |
| JP | 5762697 B2 | 6/2015 |
| JP | 5856712 B2 | 2/2016 |
| JP | 5908270 B2 | 4/2016 |
| JP | 5944331 B2 | 7/2016 |
| JP | 6050522 B2 | 12/2016 |
| JP | 2017051211 A | 3/2017 |
| JP | 2017104552 A | 6/2017 |
| JP | 6246742 B2 | 12/2017 |
| JP | 6342524 B2 | 6/2018 |
| JP | 6434495 B2 | 12/2018 |
| JP | 6445509 B2 | 12/2018 |
| JP | 6445742 B1 | 12/2018 |
| JP | 6466114 B2 | 2/2019 |
| JP | 6515084 B2 | 4/2019 |
| JP | 6528010 B1 | 5/2019 |
| JP | 6655655 B2 | 2/2020 |
| JP | 6776021 B2 | 10/2020 |
| JP | 6776025 B2 | 10/2020 |
| JP | 6786275 B2 | 11/2020 |
| JP | 6821812 B2 | 1/2021 |
| JP | 2021007772 A | 1/2021 |
| JP | 2021501011 A | 1/2021 |
| JP | 6843502 B2 | 3/2021 |
| JP | 6894004 B2 | 6/2021 |
| JP | 6920312 B2 | 8/2021 |
| JP | 6926306 B2 | 8/2021 |
| JP | 6932484 B2 | 8/2021 |
| JP | 6936872 B2 | 9/2021 |
| JP | 2021523755 A | 9/2021 |
| JP | 6980386 B2 | 11/2021 |
| JP | 2022020838 A | 2/2022 |
| WO | 9204933 A1 | 4/1992 |
| WO | 9412089 A1 | 6/1994 |
| WO | 9843530 A1 | 10/1998 |
| WO | 9906095 A2 | 2/1999 |
| WO | 0168178 A1 | 9/2001 |
| WO | 02089891 A2 | 11/2002 |
| WO | 2005113050 A1 | 12/2005 |
| WO | 2006011931 A2 | 2/2006 |
| WO | 2008091197 A1 | 7/2008 |
| WO | 2009082570 A1 | 7/2009 |
| WO | 2010035599 A1 | 4/2010 |
| WO | 2017098198 A1 | 6/2017 |
| WO | 2018053148 A1 | 3/2018 |
| WO | 2018053164 A1 | 3/2018 |
| WO | 2018136741 A1 | 7/2018 |
| WO | 2019226640 A1 | 11/2019 |

\* cited by examiner

REDUCED ACTUATION FORCE ELECTROPHYSIOLOGY CATHETER HANDLE

CROSS-REFERENCE TO RELATED APPLICATIONS

This application claims the benefit of U.S. provisional application No. 62/740,828, filed 3 Oct. 2018, which is hereby incorporated by reference in its entirety as though fully set forth herein.

BACKGROUND a. Field

The instant disclosure relates to actuators for steerable medical devices. In particular, the disclosure relates to systems and devices for reducing the actuating and locking forces of an electrophysiology catheter.

b. Background Art

Electrophysiology catheters are used in a variety of diagnostic, therapeutic, and/or mapping and ablative procedures to diagnose and/or correct conditions such as atrial arrhythmias, including for example, ectopic atrial tachycardia, atrial fibrillation, and atrial flutter. Arrhythmias can create a variety of conditions including irregular heart rates, loss of synchronous atrioventricular contractions, and stasis of blood flow in a chamber of a heart, which can lead to a variety of symptomatic and asymptomatic ailments and even death.

Typically, a catheter is deployed and manipulated through a patient's vasculature to the intended site, for example, a site within a patient's heart. The catheter typically carries one or more electrodes that can be used for cardiac mapping or diagnosis, ablation, and/or other therapy delivery modes, or both, for example. Once at the intended site, treatment can include, for example, radio frequency (RF) ablation, cryoablation, laser ablation, chemical ablation, high-intensity focused ultrasound-based ablation, microwave ablation, and/or other ablation treatments. In some procedures, the catheter imparts ablative energy to cardiac tissue to create one or more lesions in the cardiac tissue. These lesions disrupt undesirable cardiac activation pathways and thereby limit, corral, or otherwise prevent errant conduction signals that can form the basis for arrhythmias.

To position a catheter within the body at a desired site, some type of navigation must be used, such as using mechanical steering features incorporated into the catheter (or an introducer sheath). In some examples, medical personnel may manually manipulate and/or operate the catheter using the mechanical steering features.

In order to facilitate the advancement of catheters through a patient's vasculature, the simultaneous application of torque at the proximal end of the catheter and the ability to selectively deflect the distal tip of the catheter in a desired direction can permit medical personnel to adjust the direction of advancement of the distal end of the catheter and to selectively position the distal portion of the catheter during an electrophysiological procedure. The proximal end of the catheter can be manipulated to guide the catheter through a patient's vasculature. The distal tip can be deflected by a pull wire or other tension member attached or anchored at the distal end of the catheter and extending proximally to an actuator in a control handle that controls the application of tension on the pull wire. In some cases, it can be desirable to reduce the amount of force that must be applied to the actuator in order to cause deflection of the distal tip.

The foregoing discussion is intended only to illustrate the present field and should not be taken as a disavowal of claim scope.

BRIEF SUMMARY

The present disclosure describes a uni-directional, plunger-type electrophysiology catheter handle designed to reduce the input force a user must apply during deflection. A force amplifier is operatively coupled to a deflection actuator of the handle. The force amplifier can be a pulley or a system of gears. The force amplifier can increase the output force of deflection actuator by the same factor as that by which the user input force is reduced. A variable-friction autolocking system can also be used to reduce the input force a user must apply during initial deflection as compared to later deflection of the catheter.

In an embodiment, a catheter handle comprises a deflection actuator configured to cause deflection of a distal portion of a catheter from a first position to a second position; and a force amplifier coupled to the deflection actuator, the force amplifier configured to reduce an input force required to cause deflection of the distal portion of the catheter from the first position to the second position, wherein the input force is applied to the deflection actuator.

In another embodiment, a deflectable catheter comprises a catheter shaft comprising a shaft proximal end, a shaft distal end, a shaft deflectable distal portion, and at least one tension member extending from the shaft proximal end to the shaft deflectable distal portion; a deflection actuator operatively coupled to the at least one tension member; a force amplifier coupled to the deflection actuator, the force amplifier configured to reduce an input force applied to the deflection actuator to cause deflection of the shaft deflectable distal portion; and a handle housing, wherein the deflection actuator is at least partially mounted in the handle housing.

The foregoing and other aspects, features, details, utilities, and advantages of the present disclosure will be apparent from reading the following description and claims, and from reviewing the accompanying drawings.

DETAILED DESCRIPTION

Referring to FIGS. 1-10, an embodiment of a uni-directional, plunger-type catheter 10 is described. While various embodiments are described herein in the context of a uni-directional catheter, it should be recognized that the disclosed principles are equally applicable to catheters capable of deflecting in more than one direction, where at least one of the deflections is not configured to deflect in a direction opposite the deflection and beyond its "undeflected" or neutral position. It should also be noted that the principles disclosed herein are equally applicable to deflection mechanisms other than plunger-type mechanisms, although various embodiments herein are described in the context of an axially-actuated, plunger-type catheter. Further details regarding the scope of disclosure can be found in commonly owned U.S. patent application Ser. No. 14/500,809, the entire disclosure of which is incorporated herein by reference.

Figure 1:
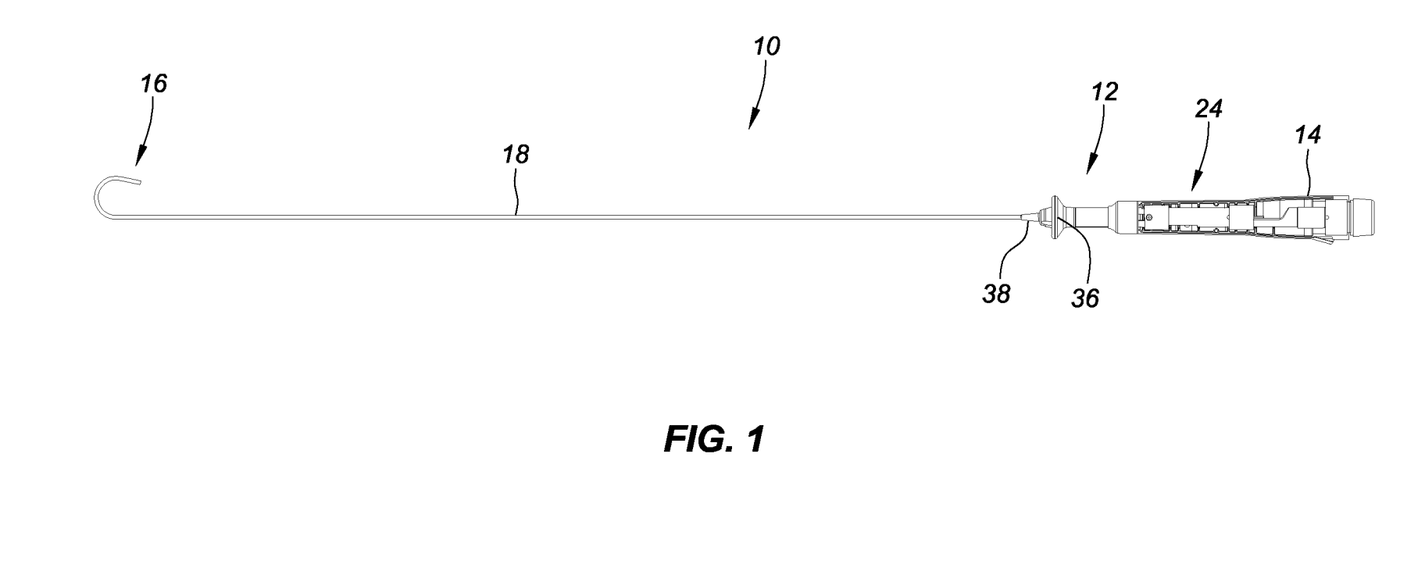
FIG. 1 depicts an example of a uni-directional catheter, shown with the upper handle housing removed and with the distal tip section in a fully-deflected configuration.

FIG. 1 depicts an embodiment of the uni-directional, plunger-type catheter 10 in a fully-actuated configuration, with the plunger assembly 12 fully advanced from (i.e., pushed distally and fully extended from) the handle housing 14, which fully deflects the distal tip section 16 of the catheter shaft 18. The plunger assembly 12 can be moved proximally and distally into and out of, respectively, the handle housing 14 as represented by the double-headed arrow 20 in FIG. 3. In the fully-actuated configuration, an active deflection element (e.g., an active tension member or pull wire or puller wire or tension strand or tension cord or tension fiber) (see, e.g., element 22 in FIGS. 5, 6, and 8) has been fully actuated (e.g., pulled to its most proximal position), thereby fully deflecting the distal tip section 16. In FIG. 1, and in FIGS. 2-10, the upper handle housing has been removed to reveal certain features inside of the handle or actuator 24.

Figure 2:
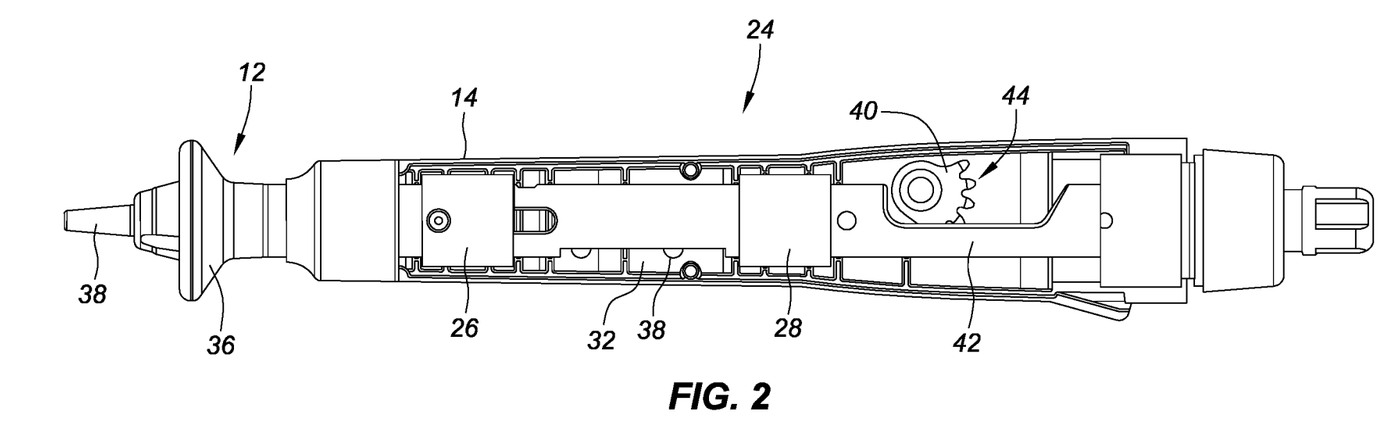
FIG. 2 is an enlarged, fragmentary view of a first embodiment of the handle depicted in FIG. 1, showing the handle in a fully retracted configuration.
Figure 3:
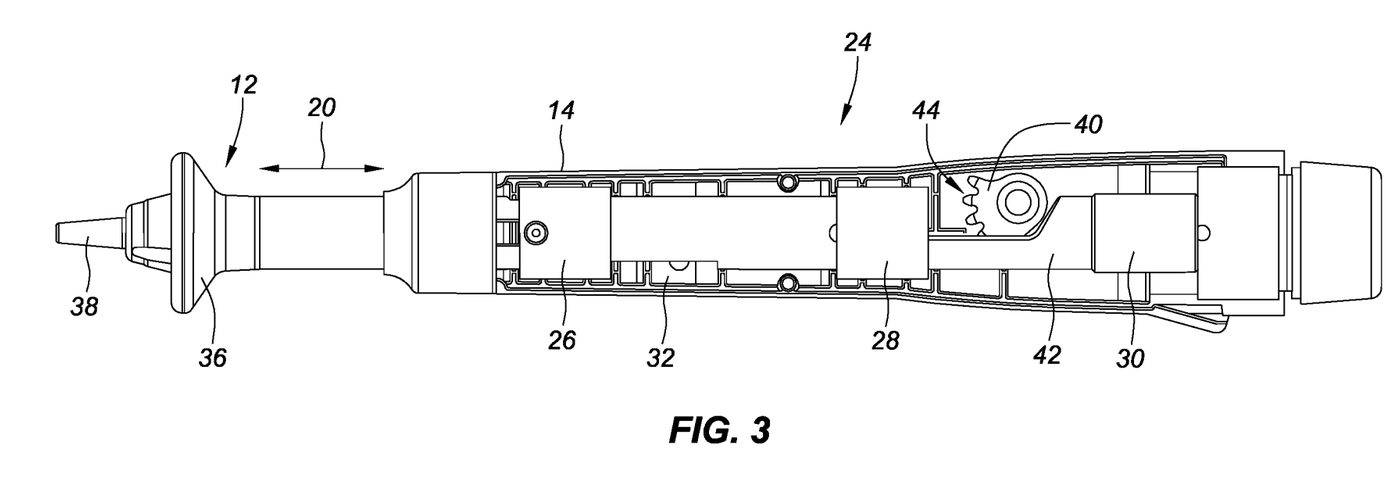
FIG. 3 is an enlarged, fragmentary view of the first embodiment of the handle depicted in FIG. 1, showing the handle in a fully actuated configuration.
Figure 4:
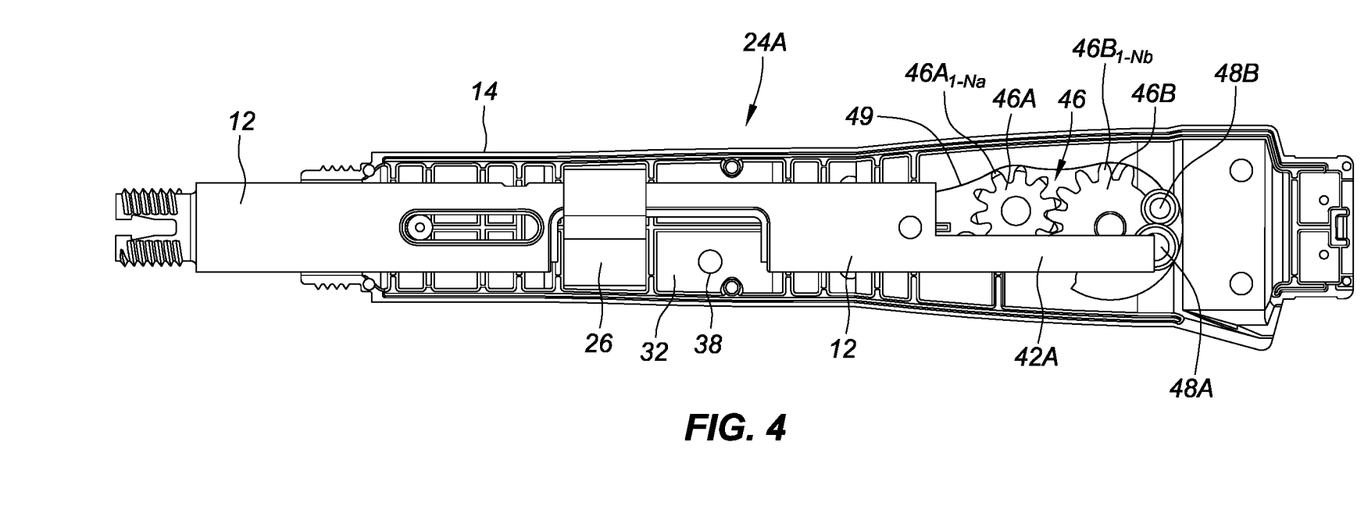
FIG. 4 is an enlarged, fragmentary view of a second embodiment of the handle depicted in FIG. 1, showing the handle in a fully retracted configuration.
Figure 5:
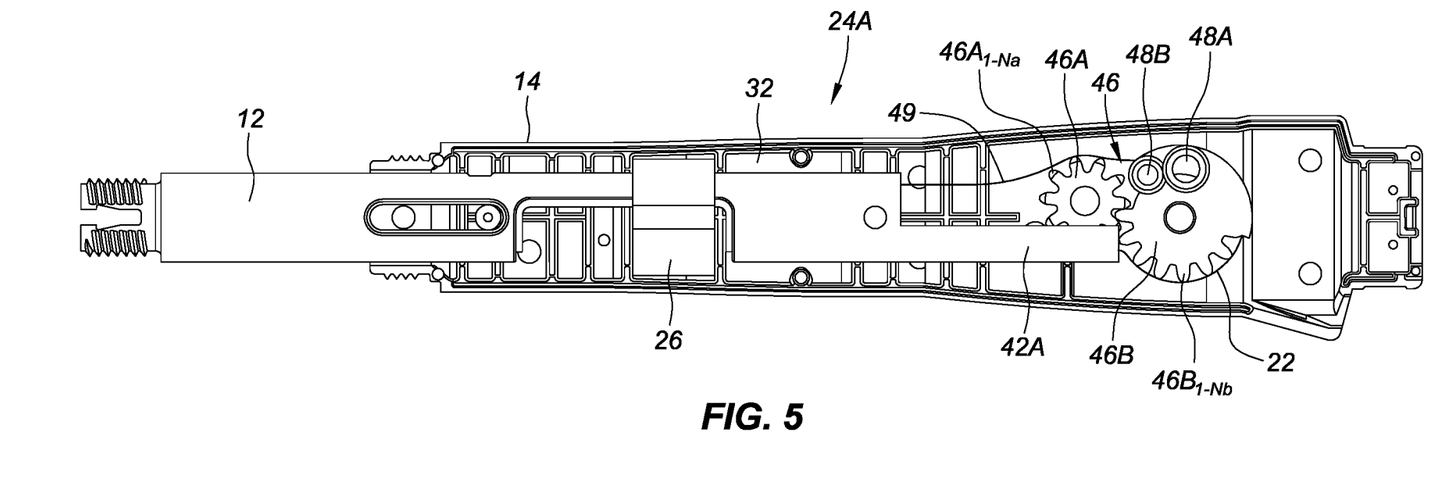
FIG. 5 is an enlarged, fragmentary view of the second embodiment of the handle depicted in FIG. 1, showing the handle in a fully actuated configuration.
Figure 6:
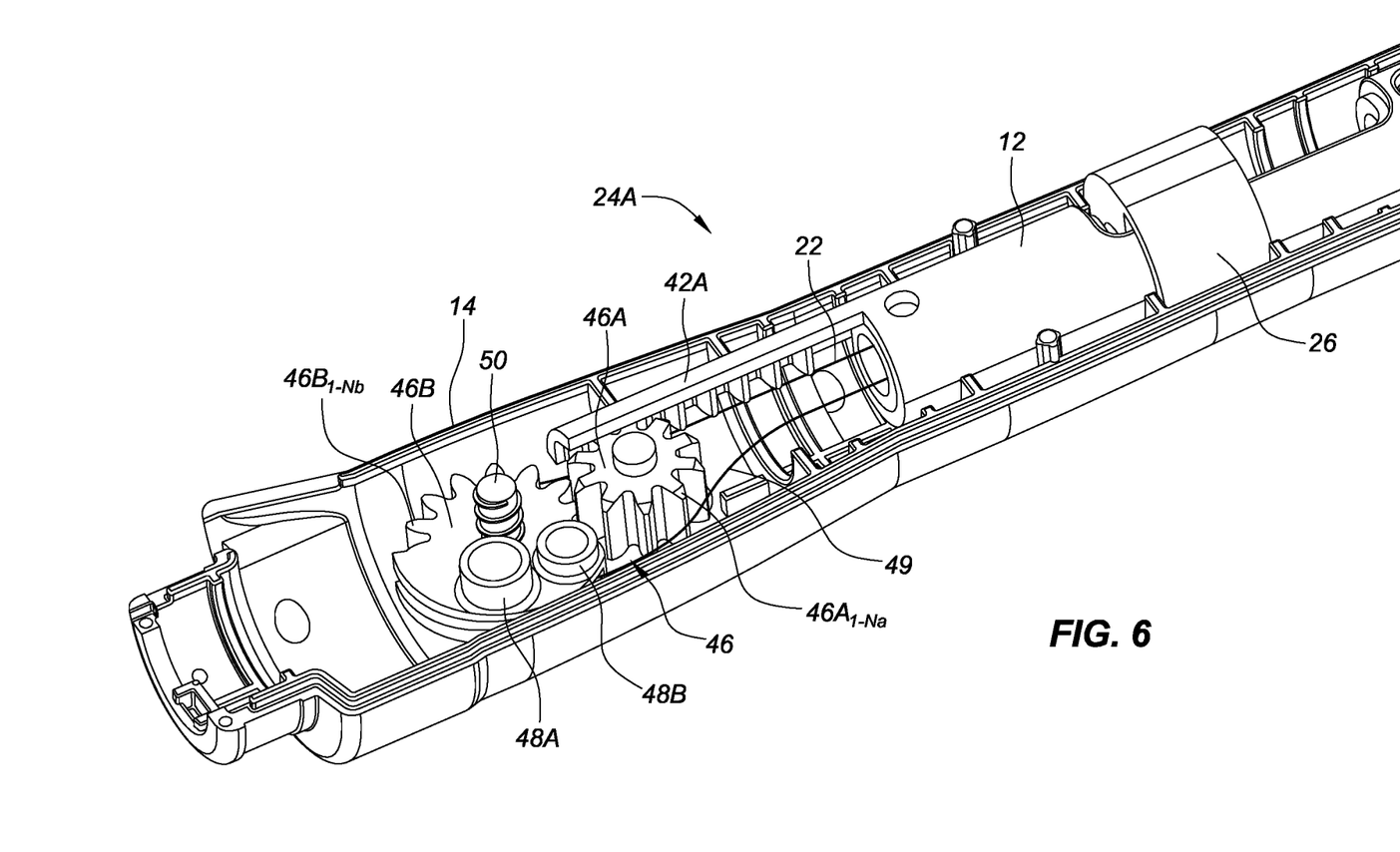
FIG. 6 is an enlarged, perspective view of the second embodiment of the handle depicted in FIG. 1, showing the handle in a fully actuated configuration.
Figure 7:
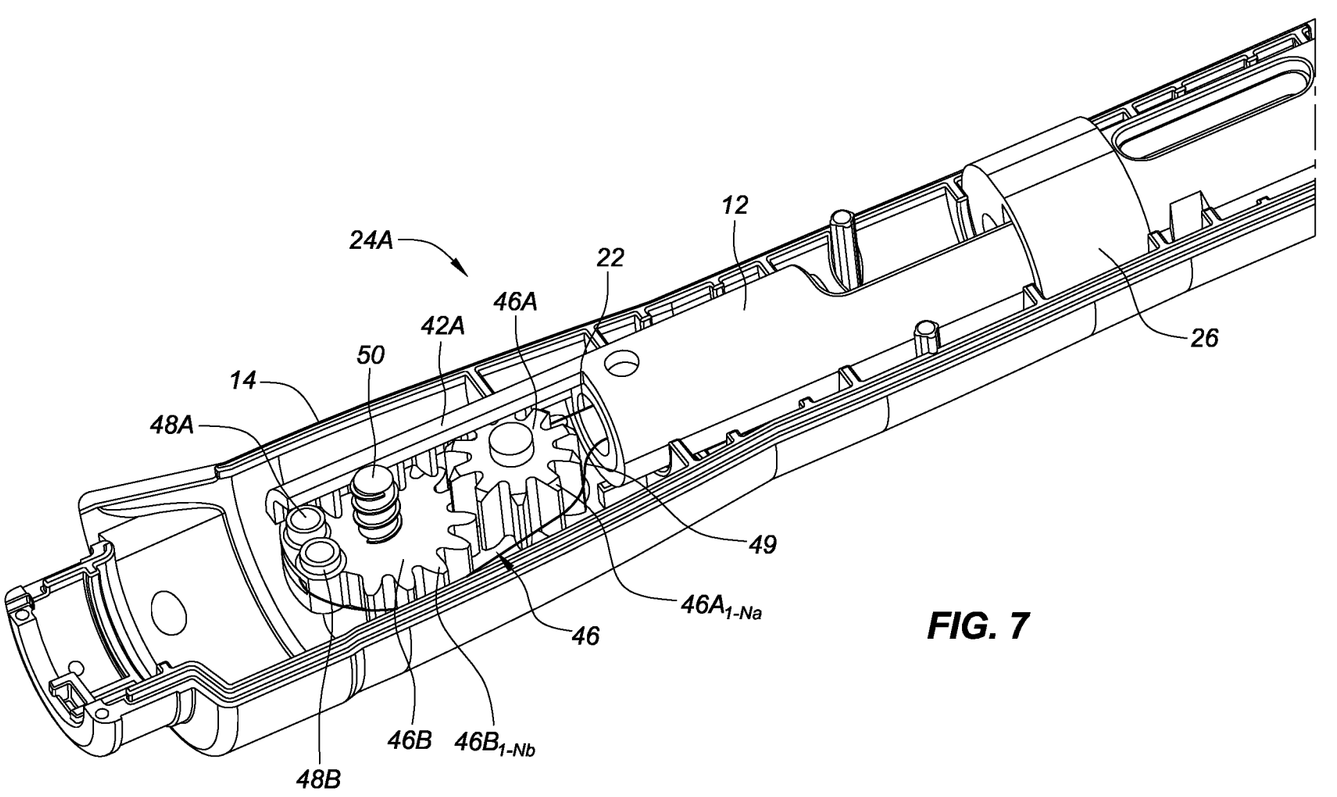
FIG. 7 is an enlarged, perspective view of the second embodiment of the handle depicted in FIG. 1, showing the handle in a fully retracted configuration.
Figure 8:
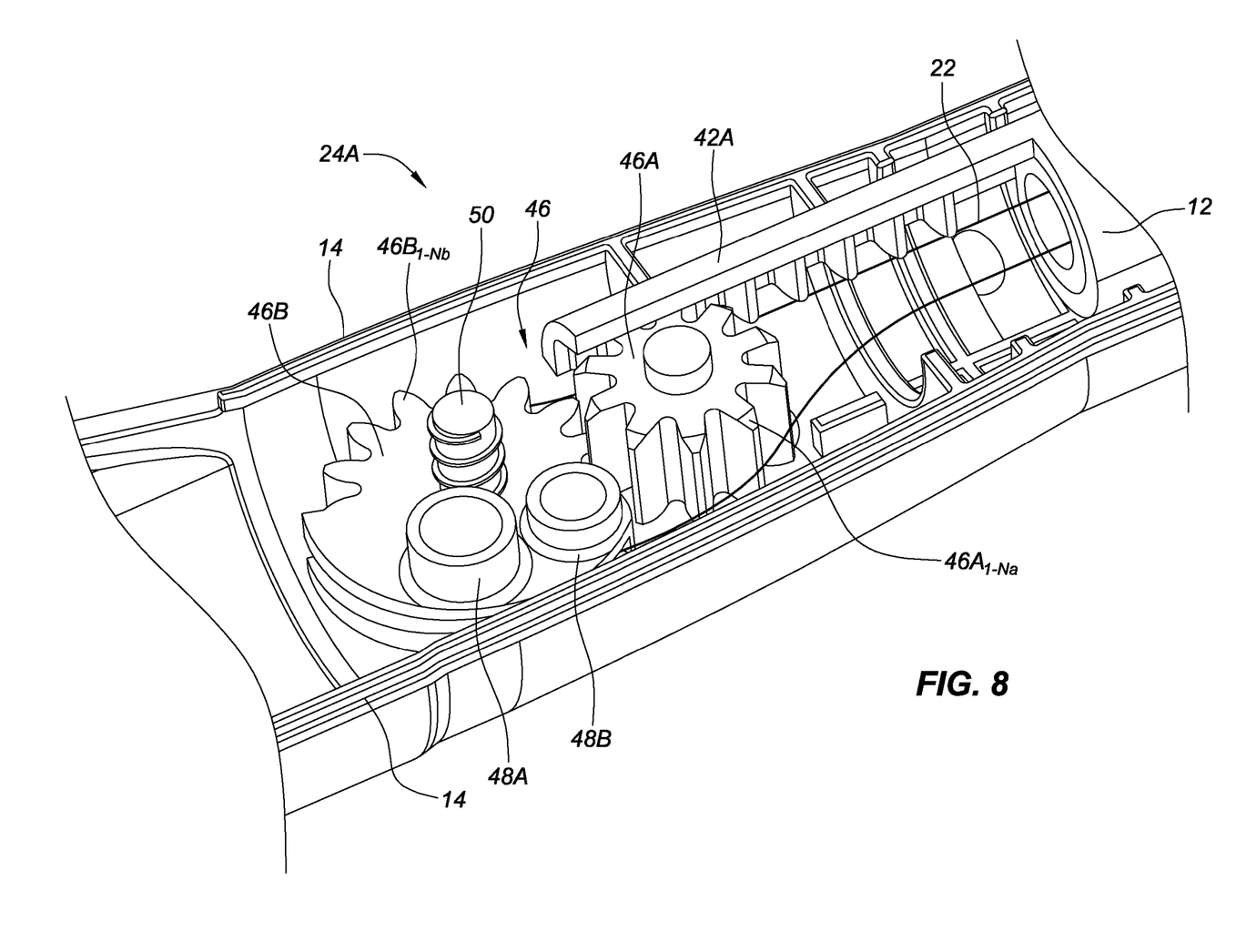
FIG. 8 is an enlarged, perspective view of the second embodiment of the handle depicted in FIG. 1, showing the position of the gear system when the handle in a fully actuated configuration.
Figure 9:
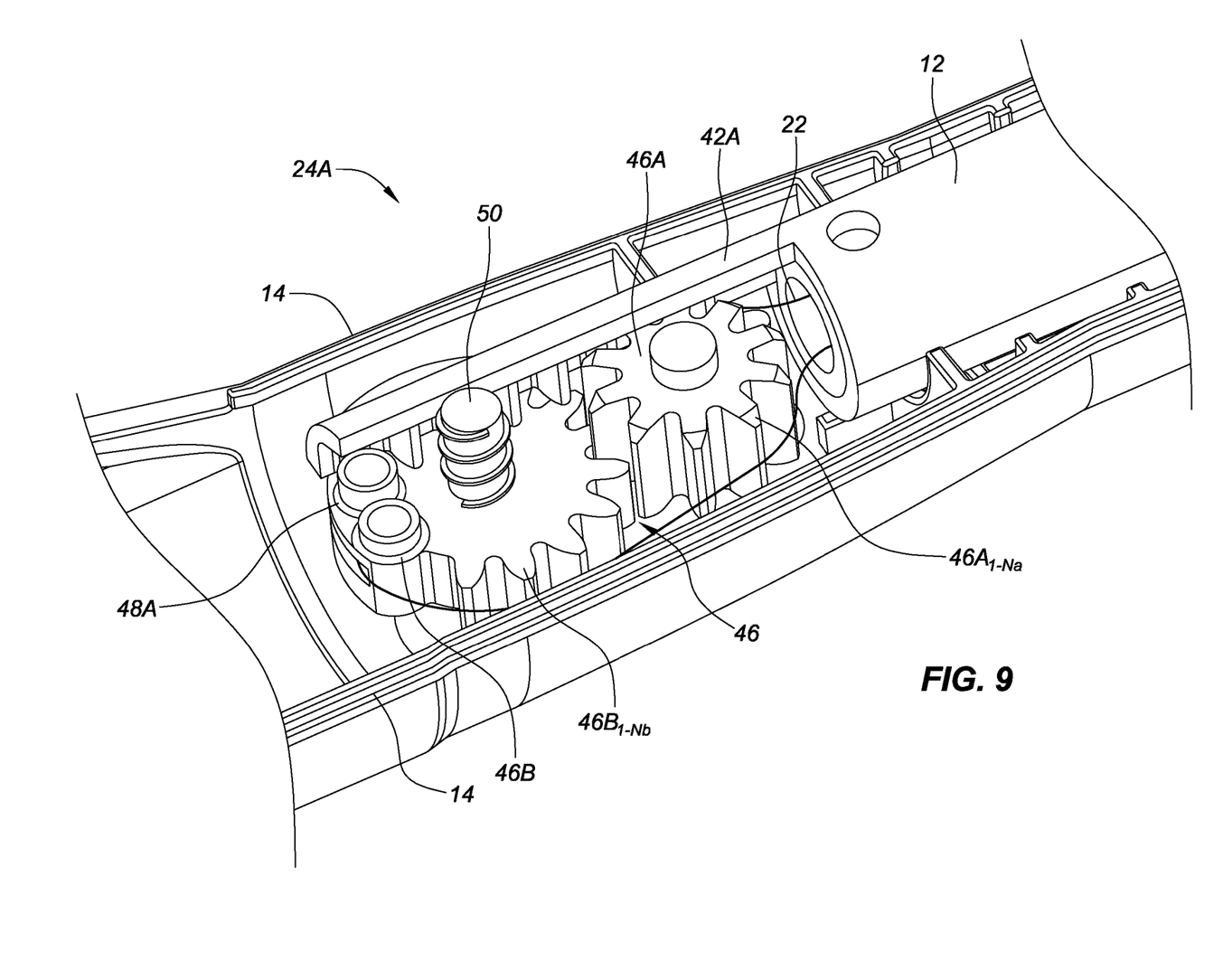
FIG. 9 is an enlarged, perspective view of the second embodiment of the handle depicted in FIG. 1, showing the position of the gear system when the handle in a fully retracted configuration.

In FIG. 2, the plunger assembly 12 has been fully retracted into the handle housing 14, and the catheter is undeflected. As shown in FIG. 3, with the plunger assembly 12 pushed distally as shown, the plunger assembly 12 is in its most distal position relative to the sleeve bearings 26, 28 slidably supporting the plunger assembly in the handle housing 14. In this position, the catheter is fully deflected (or fully actuated). A plunger cap 30 comprising the proximal part of the plunger assembly 12 may be seen in FIG. 3. A gripper 32 comprising a wire anchor 34 is visible in FIGS. 2 and 3, and shown to better advantage in FIG. 4. The gripper may be held together with the upper and lower handle housing 14, neither of which move with movement of the plunger assembly 12. At the distal end of the plunger assembly 12 is a thumb boss or thumb gripper 36. During use of the catheter, the user, most likely an electrophysiologist or other physician, will generally grip the handle housing 14 with the fingers of one hand and push or pull on the thumb boss 36 with the thumb of the gripping hand. As also shown in FIGS. 2 and 3, distal from the thumb boss is a strain relief 38, which supports the proximal portion of the catheter shaft 18.

With further references to FIGS. 2 and 3, a plunger-coupled pulley gear 40 is coupled to the proximal end of the plunger assembly 12 via a rack portion 42 of the plunger assembly 12. The rack portion 42 can be configured to engage the teeth 44 of the gear 40 when the plunger assembly is pushed distally, thereby moving the teeth in a clockwise direction. A pull wire (not shown) can be wrapped on the gear 40, and therefore can be distally released when the plunger assembly 12 is actuated.

The present disclosure implements a force-reducing demultiplication mechanism between the user-actuated push-pull plunger handle 24, as described above with respect to FIGS. 1-3, and the pull wire. The demultiplication mechanism relies on the distally oriented motion of the proximal end of the pull wire. When the plunger assembly 12 is pushed distally, from the fully retracted position shown in FIG. 2 to the fully actuated position shown in FIG. 3, the proximal end of the pull wire is "pulled," relative to the catheter shaft 18, proximally by the distance of the stroke length $L_0$ (e.g., 18 mm) of the plunger assembly 12. At the same time, the proximal end of the pull wire, which is wrapped on the plunger-coupled pulley gear 40, is released distally from the gear 40 by a length $L_1$ (e.g., 6 mm). This results in a pull wire stroke length of $L_0-L_1$ (e.g., 12 mm) and a force reduction by a factor of $L_0-L_1/L_0$ (e.g., ⅔ according to the above exemplary values). Thus, the above-described demultiplication mechanism provides a mechanical advantage and results in a difference between both plunger and pull wire stroke lengths. The plunger stroke length becomes larger than the stroke length of the pull wire by an adjustable factor (e.g., a factor of 1.5×) while the force applied by the user on the plunger is reduced by the same amount (e.g., by a factor of 1.5×).

Turning now to FIGS. 4-10, another embodiment of a handle 24A for a uni-directional catheter designed to reduce the catheter's actuating and locking forces will be described. Similar to the embodiment described above with respect to FIGS. 2 and 3, mechanical advantage is also used in this embodiment to reduce the actuating and locking forces. FIGS. 4, 7, 9, 10b, and 10e illustrate the handle 24A in its fully retracted position, similar to the handle 24 shown in FIG. 2. In this embodiment, the proximal end of a first (or main) pull wire 22 is connected to a system of gears 46, including a smaller gear 46A and a larger gear 46B. The proximal end of the plunger assembly 12 comprises a rack portion 42A, similar to the rack portion 42 shown in FIGS. 2 and 3. The rack portion 42A can be configured to engage the teeth $46A_{1-Na}$ of the smaller gear 46A, which in turn can engage the teeth $46B_{1-Nb}$ of the larger gear 46B. The first pull wire 22 can be attached to the larger gear 46B via a first location hole 48A.

When a user pushes the plunger assembly 12 distally, while holding the handle 24A, the smaller gear 46A may rotate in the clockwise direction, which in turn rotates the larger gear 46B in the counterclockwise direction. Counterclockwise rotation of the larger gear 46B, including the location hole 48A, results in the first pull wire 22 being pulled in the proximal direction, thereby deflecting the catheter. FIGS. 5, 6, 8, and 10d illustrate the positioning of the system of gears 46, as well as the plunger assembly 12, when the handle 24A is fully actuated and the catheter is fully deflected.

The above-described motion of the plunger assembly 12, including the rack portion 42A, and the system of gears 46 results in a mechanical advantage which allows the user to apply less actuation force in order to pull the first pull wire 22. This mechanical advantage (MA) can be calculated as follows:

$$MA=N_B/N_A$$

where $N_A$ is the number of teeth on the smaller gear 46A and $N_B$ is the number of teeth on the larger gear 46B. If $N_B>N_A$, the output force from the larger gear 46B is amplified with respect to the input force to the smaller gear 46A. Thus, the input force is less than the output force in the same ratio (e.g., the input force decreases by a factor of X and the output force increases by a factor of X). This amplification in output force provides an advantage by allowing the user to apply less force to push the plunger assembly 12 distally and deflect the catheter.

With continued reference to FIGS. 4-10, an opposite deflection direction and a return to straight mechanism for catheter handle 24A will now be described. A second pull wire 49 can be connected to the larger gear 46B via a second location hole 48B, which may be smaller than and adjacent to the first location hole 48A. Thus, when the larger gear 46B is rotated in the clockwise direction, the second pull wire 49 is pulled in the proximal direction. This, in turn, results in deflection of the catheter in the opposite direction to the deflection direction of the first pull wire 22. Similarly, when the plunger assembly 12 is moved proximally back to its neutral position, the larger gear 46B will rotate in the counterclockwise direction and will pull the second pull wire 49 in the distal direction, bringing the catheter tip back to straight.

With reference to FIGS. 6-10, a variable autolock system will be now described. Existing autolock systems lock the plunger assembly 12 wherever it is left and keep the catheter deflected accordingly. For example, a known autolock system is implemented by adding a pre-calculated amount of friction to the moving component of the handle (e.g., the plunger assembly 12). This added friction remains the same for the whole actuation period, and it increases the force required to push the plunger assembly distally.

The present inventors have contemplated a new design for an autolock system that does not involve adding a pre-calculated amount of friction to the moving component of the handle throughout the actuation period. Instead, a low amount of friction is applied to the plunger assembly 12 when the plunger assembly is in a neutral (e.g., fully retracted) position, as shown in FIGS. 4, 7, 9, 10b, and 10e. The amount of friction applied to the plunger assembly 12 increases as the plunger assembly 12 is pushed outwards in the distal direction, as shown in FIGS. 5, 6, and 8, 10a, and 10d. This helps the user apply less force during initial movement of the plunger assembly 12 as compared to its later movement.

The above-described variable-friction autolocking system can be achieved by using a threaded central axel 50 of around which the larger gear 46B rotates, as shown in FIGS. 6-10. As shown in FIGS. 10a, b, d, and e, a frictional element (e.g., a ring, such as an O-ring, or a disc) 51 can be placed between the bottom surface of the larger gear 46B and the top surface of a boss feature 14A of the handle housing 14. In an embodiment, the bottom surface of the larger gear 46B can include a pocket area 52 to accommodate the frictional element 51, as illustrated in FIG. 10c. As the larger gear 46B rotates around the threaded central axel 50, the threads force the gear to translate up or down according to the direction of the threads. When the larger gear 46B rotates in the counterclockwise direction it moves downwards, and when the larger gear 46B rotates in the clockwise direction it moves upwards.

Figure 10A:
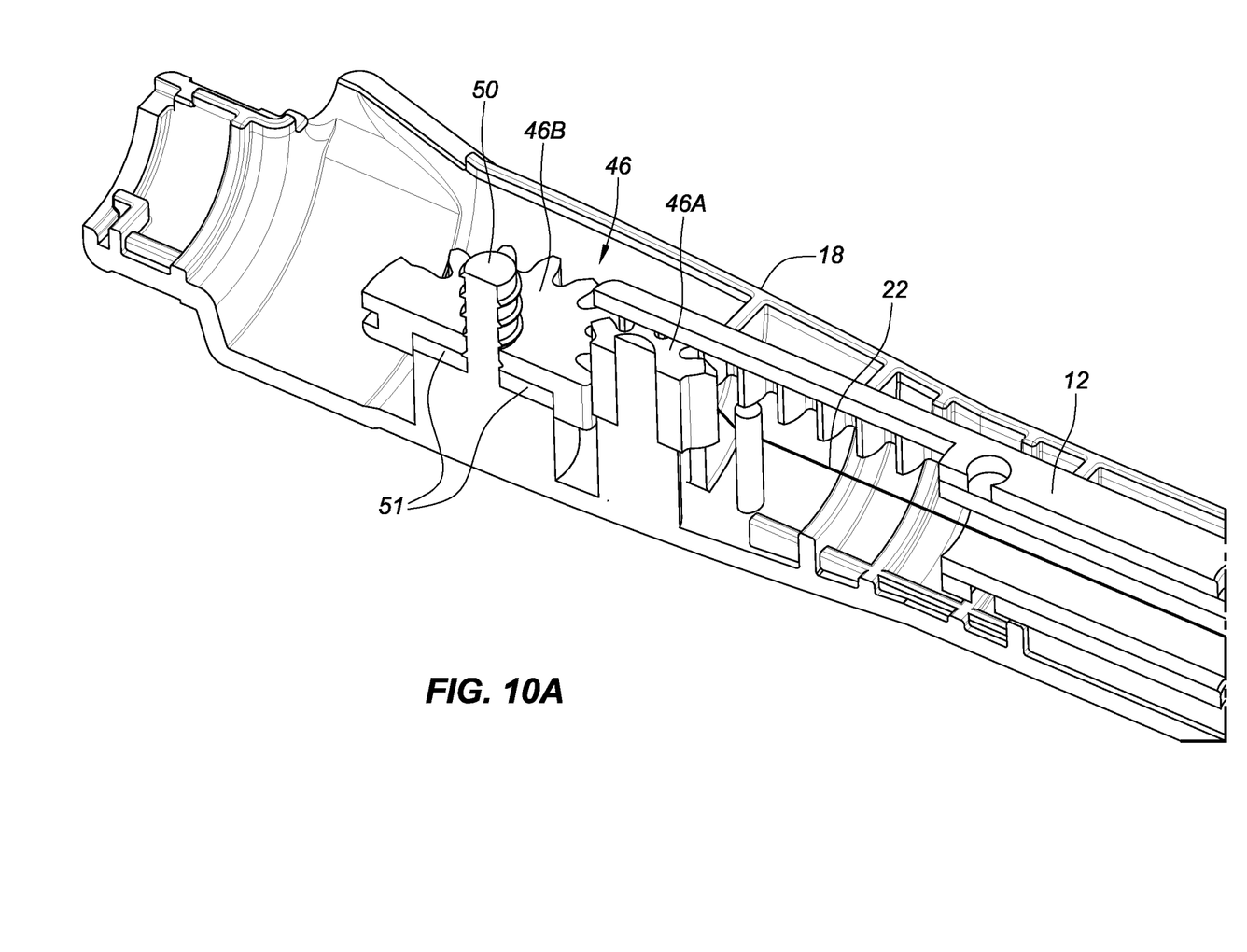
FIG. 10a is an enlarged, cross-sectional view of the second embodiment of the handle depicted in FIG. 1, showing the position of the gear system when the handle in an actuated configuration.
Figure 10B:
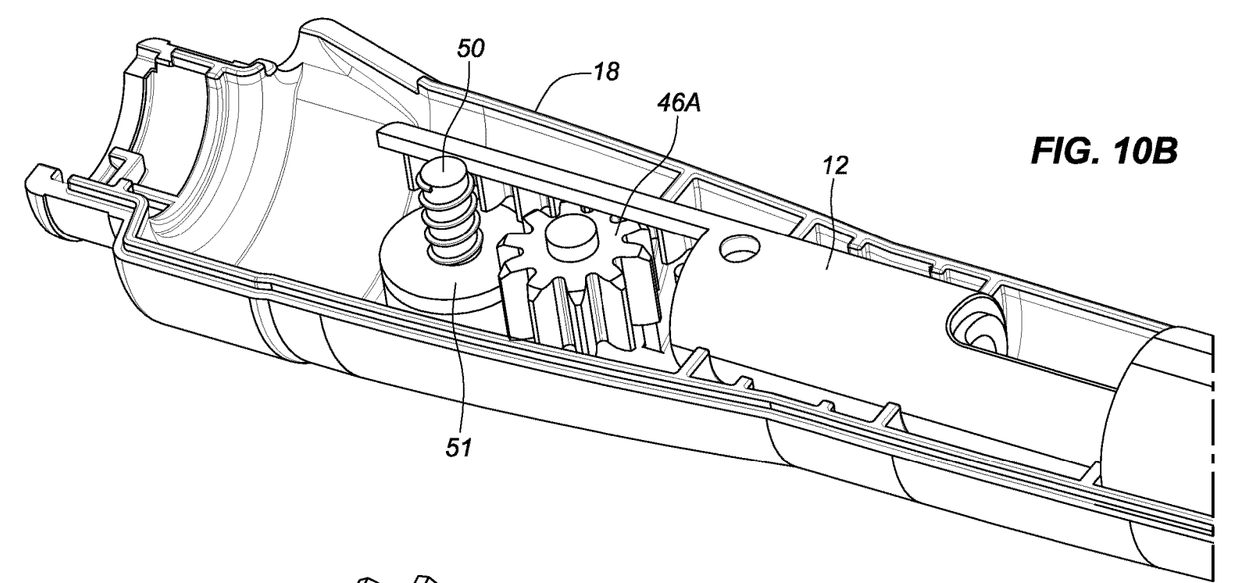
FIG. 10b is an enlarged, perspective view of the second embodiment of the handle depicted in FIG. 1, in a fully retracted configuration, with the larger gear removed to show the frictional element.
Figure 10C:
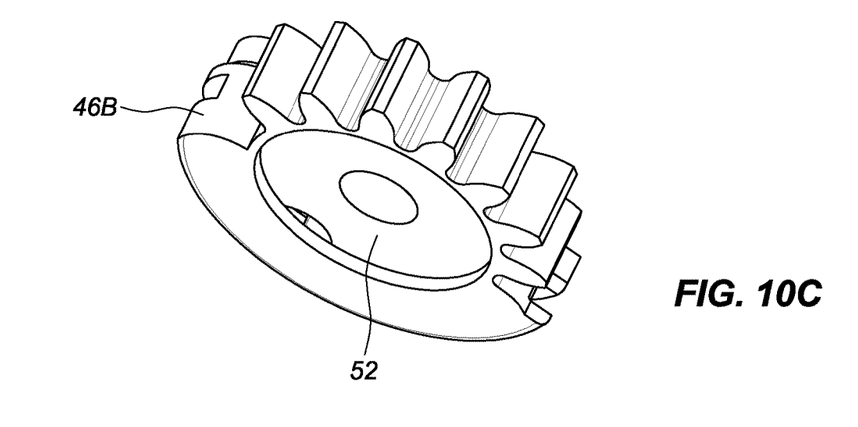
FIG. 10c is an enlarged, bottom view of the larger gear that has been removed in FIG. 10b.
Figure 10D:
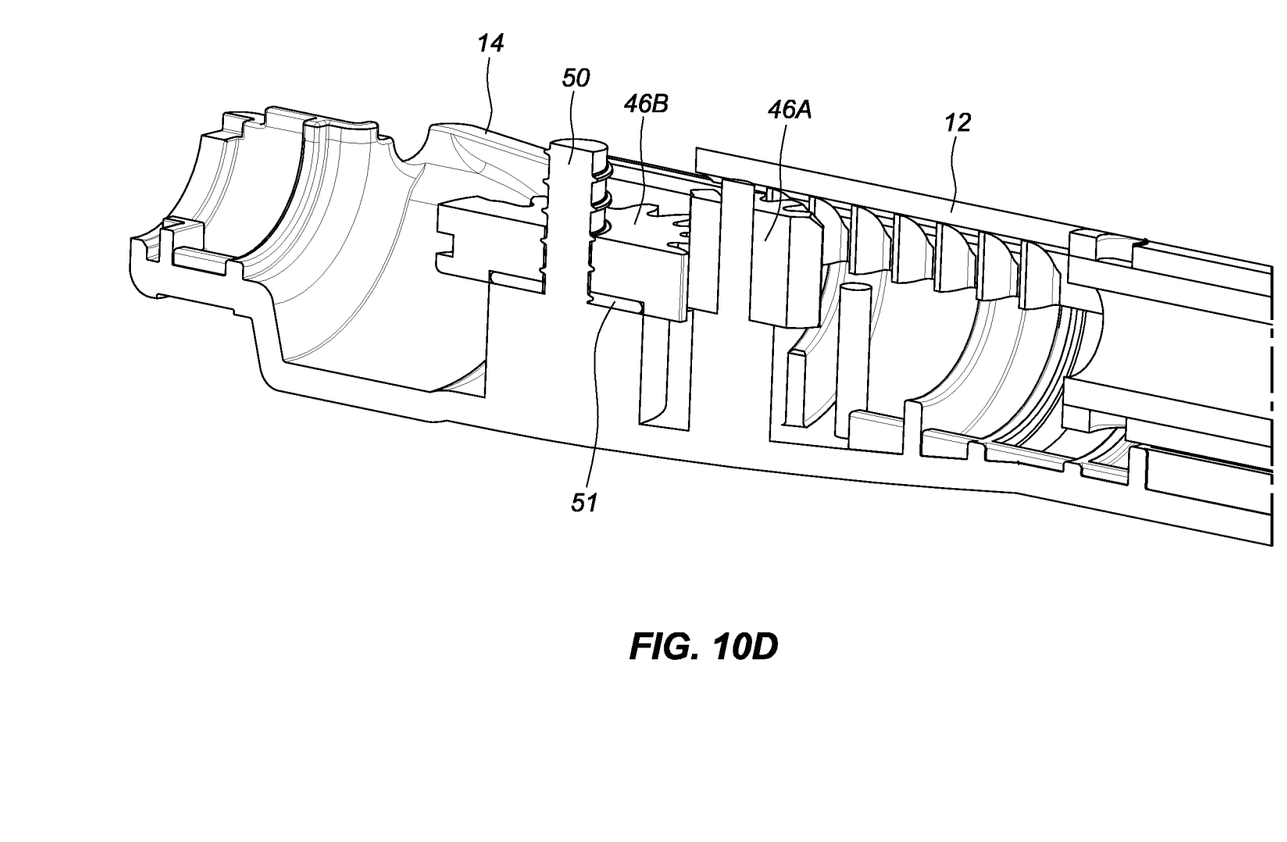
FIG. 10d is an enlarged, cross-sectional view of the second embodiment of the handle depicted in FIG. 1, showing the frictional element when the handle in a fully actuated configuration.
Figure 10E:
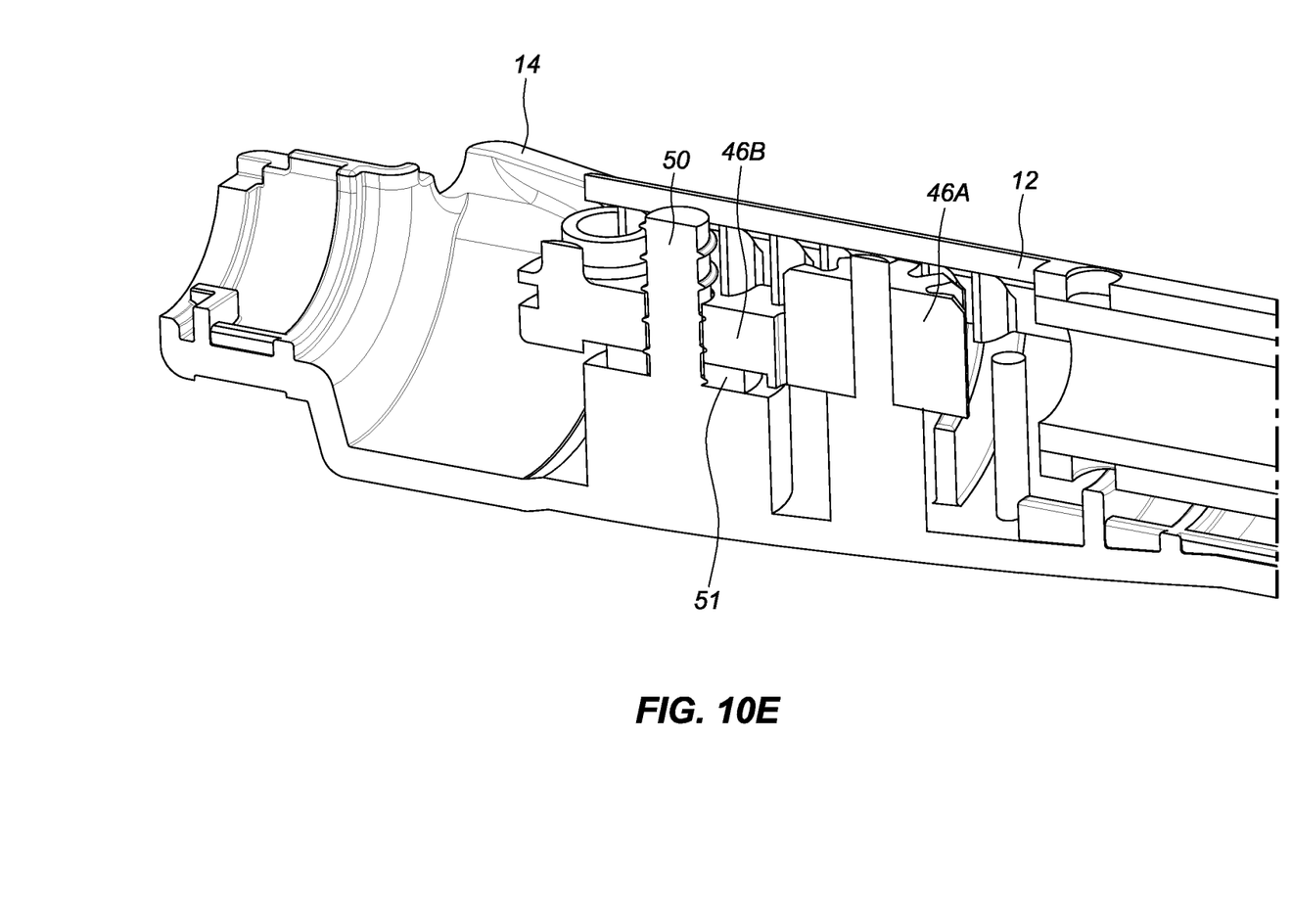
FIG. 10e is an enlarged, cross-sectional view of the second embodiment of the handle depicted in FIG. 1, showing the frictional element when the handle in a fully retracted configuration.

Because the frictional element 51 is positioned at the bottom surface of the larger gear 46B, when the larger gear 46B moves downwards (e.g., rotates in the counterclockwise direction, which results in actuation of the first pull wire 22), as shown in FIG. 10d, the amount of friction between the frictional element 51 and the bottom surface of the larger gear 46B (e.g., the portion of the bottom surface of the larger gear 46B located with the pocket area 52) increases. This increase in friction provides a locking mechanism to keep the plunger assembly 12 in the actuated position. Thus, as the plunger assembly 12 is pushed distally and the first pull wire 22 is pulled proximally, the amount of force a user must apply to move the plunger assembly 12 increases. Similarly, when the larger gear 46B moves upwards (e.g., rotates in the clockwise direction, which results in actuation of the second pull wire 49), as shown in FIG. 10e, the amount of friction between the frictional element 51 the bottom surface of the larger gear 46B (e.g., the portion of the bottom surface of the larger gear 46B located with the pocket area 52) decreases. Thus, when the plunger assembly is returned to its neutral position, or pulled proximally, and the second pull wire 49 is pulled proximally, the amount of force a user must apply to move the plunger assembly 12 decreases.

Although at least one embodiment of a reduced actuation force catheter handle has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and can include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure can be made without departing from the spirit of the disclosure as defined in the appended claims.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A catheter handle comprising:
   a handle housing having a proximal end and a distal end;
   a plunger assembly configured to be moved proximally out of the distal end of the handle housing and distally into the distal end of the handle housing, wherein the plunger assembly is configured to cause deflection of a distal portion of a catheter from a first position to a second position; and
   a force amplifier coupled to the plunger assembly, the force amplifier configured to reduce an input force required to cause deflection of the distal portion of the catheter from the first position to the second position, wherein the input force is applied to the plunger assembly,
      wherein the force amplifier comprises a system of gears, the system of gears comprising at least a first gear and a second gear; and
      wherein the force amplifier comprises a threaded central axel around which the second gear rotates;
      wherein the threaded central axel is configured to cause the second gear to translate upwards or downwards based on a direction of rotation of the second gear; and
   a frictional element located between a bottom surface of the second gear and a bottom portion of the catheter handle, wherein the frictional element is an O-ring;
      wherein friction between the frictional element and the bottom surface of the second gear increases as the second gear moves downwards; and
      wherein friction between the frictional element and the bottom surface of the second gear decreases as the second gear moves upwards.

2. The catheter handle of claim 1, wherein the force amplifier is further configured to increase an output force of the plunger assembly; and
   wherein the output force comprises tension applied to a first pull wire coupled to the plunger assembly and to the distal portion of the catheter.

3. The catheter handle of claim 2, wherein the input force is reduced by a factor X and the output force is increased by the factor X.

4. The catheter handle of claim 2, wherein the plunger assembly is configured to apply tension to the first pull wire when the plunger assembly is advanced distally relative to a housing of the handle housing.

5. The catheter handle of claim 2, wherein the force amplifier comprises a pulley; and
   wherein a distal end of the first pull wire is attached to the pulley.

6. The catheter handle of claim 2,
   wherein the first gear is coupled to the plunger assembly and to the second gear.

7. The catheter handle of claim 6, wherein the first gear has a first number of teeth and the second gear has a second number of teeth; and
   wherein the second number of teeth is greater than the first number of teeth.

8. The catheter handle of claim 6, wherein a distal end of the first pull wire is attached to the second gear at a first location along an outer diameter of the second gear.

9. The catheter handle of claim 8, wherein a second pull wire is attached to the second gear at a second location along the outer diameter of the second gear, the second location being opposite the first location.

10. The catheter handle of claim 9, wherein tension applied to the first pull wire results in deflection of the catheter in a first direction, tension applied to the second pull wire results in deflection of the catheter in a second direction, and the first direction is opposite the second direction.

11. The catheter handle of claim 1, wherein the input force increases as the second gear moves downwards; and wherein the input force decreases as the second gear moves upwards.

12. A deflectable catheter comprising:

a catheter shaft comprising a shaft proximal end, a shaft distal end, a shaft deflectable distal portion, and at least one tension member extending from the shaft proximal end to the shaft deflectable distal portion;

a plunger assembly operatively coupled to the at least one tension member;

a force amplifier coupled to the plunger assembly, the force amplifier configured to reduce an input force applied to the plunger assembly to cause deflection of the shaft deflectable distal portion, wherein the force amplifier comprises a system of gears, the system of gears comprising at least a first gear and a second gear; and wherein the force amplifier comprises a threaded central axel around which the second gear rotates;

wherein the threaded central axel is configured to cause the second gear to translate upwards or downwards based on a direction of rotation of the second gear; and a frictional element located between a bottom surface of the second gear and a bottom portion of the catheter handle, wherein the frictional element is an O-ring;

wherein friction between the frictional element and the bottom surface of the second gear increases as the second gear moves downwards; and wherein friction between the frictional element and the bottom surface of the second gear decreases as the second gear moves upwards; and a handle housing having a proximal end and a distal end, wherein the plunger assembly is configured to be moved proximally out of the distal end of the handle housing and distally into the distal end of the handle housing.

13. The deflectable catheter of claim 12, wherein the force amplifier is further configured to increase an output force of the plunger assembly.

14. The deflectable catheter of claim 13, wherein the input force is reduced by a factor X and the output force is increased by the factor X.

15. The deflectable catheter of claim 12, wherein the plunger assembly is configured to apply tension to the at least one tension member when the plunger assembly is advanced distally relative to the handle housing.

16. The deflectable catheter of claim 12, wherein the force amplifier comprises a pulley; and wherein a distal end of at least one tension member is attached to the pulley.

17. The deflectable catheter of claim 12, wherein the first gear is coupled to the plunger assembly and to the second gear.

18. The deflectable catheter of claim 14, wherein the first gear has a first number of teeth and the second gear has a second number of teeth; and wherein the second number of teeth is greater than the first number of teeth.

\* \* \* \* \*